US011179415B1

United States Patent
Madray

(10) Patent No.: US 11,179,415 B1
(45) Date of Patent: Nov. 23, 2021

(54) PROCESS OF USING CHLORINE DIOXIDE FOR THE ATTENUATION AND/OR TREATMENT OF CORONAVIRUS DISEASES SUCH AS COVID-19 AND DISABLING, TREATING OR ATTENUATING THE SARS COV-2 VIRUS, AND ITS FUTURE INFECTIVE VARIANTS

(71) Applicant: George William Madray, Brunswick, GA (US)

(72) Inventor: George William Madray, Brunswick, GA (US)

( * ) Notice: Subject to any disclaimer, the term of this patent is extended or adjusted under 35 U.S.C. 154(b) by 0 days.

(21) Appl. No.: 17/127,655

(22) Filed: Dec. 18, 2020

(51) Int. Cl.
| | |
|---|---|
| *A61K 33/20* | (2006.01) |
| *A61K 9/00* | (2006.01) |
| *A61K 47/10* | (2017.01) |
| *A61K 45/06* | (2006.01) |
| *A61K 9/08* | (2006.01) |

(52) U.S. Cl.
CPC ............ *A61K 33/20* (2013.01); *A61K 9/0043* (2013.01); *A61K 9/0078* (2013.01); *A61K 9/08* (2013.01); *A61K 45/06* (2013.01); *A61K 47/10* (2013.01)

(58) Field of Classification Search
CPC ............ A61K 33/20; A61K 9/08; A61P 31/12
See application file for complete search history.

(56) References Cited

U.S. PATENT DOCUMENTS

2016/0074432 A1\* 3/2016 Alliger ............... A61K 2300/00
424/600

FOREIGN PATENT DOCUMENTS

CN 106074692 A \* 11/2016

OTHER PUBLICATIONS

Akamatsu et al (Journal of Occupational Medicine and Toxicology, 2012, vol. 7, pp. 1-8) (Year: 2012).\*
US Department of Health and Human Services (HHS), 2004, Toxicological Profile for Chlorine Dioxide and Chlorite, pp. i-xix and 1-143 and appendices) (Year: 2004).\*
Safety Data Sheet (Chlorine dioxide gas, revision Oct. 6, 2015) (Year: 2015).\*
Gilmour (The Charlotte Observer, Miracle remedy won't cure autism or HIV: It's bleach and may kill you, FDA warns; Aug. 2019 article) (Year: 2019).\*
Ma et al (International Journal of Environmental Research and Public Health, Mar. 2017, vol. 14, pp. 329) (Year: 2017).\*
Burton et al (Cochrane Library, 2020, pp. 1-42) (Year: 2020).\*
CN 106074692 (Espacenet English translation, downloaded May 2021) (Year: 2021).\*
Landau (EverydayHealth, Rock the Netl Pot: 6 Smart Nasal Irrigation Tips to Promote Sinus Health and Minimize Sinus Infections, Oct. 11, 2018, https://www.everydayhealth.com/sinus-infection/irrigating-your-sinuses-with-neti-pots-nose-sprays/) (Year: 2018).\*
Zambrano-Estrada et al (bioRxiv, Nov. 10, 2020, abstract) (Year: 2020).\*

\* cited by examiner

*Primary Examiner* — Mark V Stevens

(57) ABSTRACT

The use of chlorine dioxide (CLO2) to kill or disable pathogens such as viruses, particularly those of the Coronavirus family. A certain amount of CLO2 is used via different modalities, particularly through one's nose or mouth, as a therapeutic. CLO2 can treat, cure and/or prevent diseases, such as methicillin resistant *Staphylococcus aureus* (MRSA), fungal infections, the common cold, and more particularly a current disease in the year 2020, known as COVID-19. The invention will not only kill or disable SARS CoV-2, which causes COVID-19, but will also kill or disable the next Coronavirus, SARS CoV-3, once CoV-2 mutates and escapes any vaccine against it.

19 Claims, No Drawings

PROCESS OF USING CHLORINE DIOXIDE FOR THE ATTENUATION AND/OR TREATMENT OF CORONAVIRUS DISEASES SUCH AS COVID-19 AND DISABLING, TREATING OR ATTENUATING THE SARS COV-2 VIRUS, AND ITS FUTURE INFECTIVE VARIANTS

Process of using chlorine dioxide solution as a safe and effective therapy for the prevention and or treatment of the Coronavirus family of diseases such as the common cold, and COVID-19, and for killing the SARS CoV-2 virus, its future mutants and diseases via the nasal and sinus passages of the upper respiratory tract and lungs of the lower respiratory tract via one's nose.

BACKGROUND OF THE INVENTION

As the world goes more into entropy, diseases become more and more difficult to cope with and to treat, particularly as they spread wildly and become immune to our modern medicines. Microbes mutate into novel pathogens that have never before been seen. A perfect example is the new SARS CoV-2. It is very contagious, even though it is not as deadly as its matriarch, SARS CoV. It is currently believed that the SARS CoV-2 from the spring of 2020 has now mutated and is now more contagious as of the fall of 2020.

It takes time to develop treatments such as antibiotics and vaccines. When they are developed, many individuals will not take them for various reasons. Microorganisms develop an immunity to many antibiotics and vaccines. So, what is much desired, is a treatment that that can be microbiocidal, that organisms cannot develop immunity against. What was considered treatable in the past is not now. We now have tuberculosis that has become antibiotic resistant, as well as certain Staphylococci such as methicillin resistant *Staphylococcus aureus* (MRSA). Viruses mutate rendering a newly developed vaccine worthless. When a virus becomes different, it is considered to be novel, and there is no vaccine to fight it.

Vaccines in particular, have genetic information that is used to disrupt the synthesis of a virulent virus. Through their genetic code, via DNA, which is double stranded or RNA which is single stranded, the virus binds to a normal healthy cell, infiltrates its nucleus, and takes over manufacturing viruses until the host cell explodes. The virus gives coded instruction, via the sequence of its base pairing to make viruses rather than the normal healthy host cells. If the code is altered or replaced by another purine or pyrimidine base, it will be considered mutated.

In the case of a mutated single stranded, RNA virus such as SARS CoV-2, any vaccine that binds to the base sequence can be hindered from doing so. Depending on where the mutation is located, a vaccine can be hindered or prevented from rendering or making the mutated virus inoperable.

In past epidemics and pandemics from the Spanish flu of 1917, to the current pandemic of COVED-19, therapeutic agents have been used to ameliorate the accompanying suffering, and death. In 1917, doctors would obtain antibodies from the plasma, after the whole blood had been centrifuged. It was obtained from those who had contracted the Spanish flu and survived it. They would then give it to others, who were then able to fight off the flu. Concerning HIV virus different cocktails of several therapeutics were used to combat the virus and it worked against AIDS. With Ebola, Remdesivir was used to prevent viral replication in fighting it.

Currently Remdesivir and Decadron are being used to fight SARS CoV-2 and are the only therapeutic agents being used to ameliorate the conditions caused by COVID-19, to date. What is needed is not just a therapeutic that makes conditions better after contracting SARS CoV-2, but something to kill it and to prevent the sickness of COVID-19 altogether!

OBJECT OF THE INVENTION

The main object of the invention is to provide a safe and inexpensive method for the treatment of different pathogens that are becoming more resistant to drugs and vaccines and are appearing at an increasing rate. For some pathogens there are no good treatments or there are poor treatments. This would be for bacteria that has developed immunity such as MRSA, stubborn fungi, on or in the body such as with fungi causing chronic sinus and respiratory conditions.

A particular object of the invention is to treat current viruses that cause the common cold, as well as those viruses that can cause respiratory conditions, such as MERS, SARS, and COVID-19.

Another object of the invention is to work with other therapeutics in killing or disabling pathogens or exposing pathogens so other therapeutics or vaccines can work more efficiently.

Another object of the invention to enable the CLO2, the active ingredient, to be readily available at a necessary concentration and for a necessary time, for the treatment of various pathological conditions.

Another object of the invention is to make the CLO2 non-irritating, non-inflammatory, yet also allowing for the infiltration, penetration, and diffusion of it to into multiple areas.

Yet another object of the invention is to be able to manufacture the CLO2 therapeutic anywhere in the world as a kit of solutions and/or ingredients and simply mixing them together, with no electricity, nor prior training in doing so.

Finally, it is an object of the invention to have a therapeutic against Coronavirus diseases that is inexpensive and does not require refrigeration or freezing while being transported as potential Coronavirus vaccines require at this time.

The foregoing objects of the invention and other objects of the invention can be gleaned from the following.

BRIEF SUMMARY OF THE INVENTION

The invention has as its active ingredient CLO2. $CLO_2$ was discovered by Sir Humphrey Davy in 1811. He produced it by acidifying potassium chlorate with sulfuric acid. In 1940 M. C. Taylor produced $CLO_2$ by adding an acid or chlorine to Sodium Chlorite. It is by the formation of $CLO_2$ from chlorite that drinking water treatment is currently practiced. $CLO_2$ has been used as a mouthwash, by the acidification of chlorite since the 1980s, and by the reaction of chlorine (Clorox™) with chlorite since the early 1990s. In the late-1990s, this inventor discovered a method of forming $CLO_2$ by the reaction of potassium iodide with chlorite as shown in U.S. Pat. No. 6,231,830.

$CLO_2$ is probably the most extensively tested disinfectant in history. This is because not much was known about it. It is a safe and effective biocide, and has been used for disinfecting, and eliminating odors in water for about 90 years; and nearly as long for whitening in the paper making industry. It has also been used for biofilm control in commercial water-cooling towers. It is used there because of its ability to oxidize pathogens through biofilm. This property is what makes it particularly useful for killing pathogens in the mucous lined nasal and sinus cavities. Finally, it is used to kill HIV and keep blood purified so as the blood can be used safely in transfusions.

It is in the nose, throat, nasal and sinus cavities, the upper respiratory tract (URT), that the Coronavirus SARS CoV-2 incubates, much as the Coronavirus that causes the common cold does. One third of patients do not have any signs or symptoms such as malaise, cough, or sore throat, and fever is absent in 75% of people during this phase and are not able to detect anything being wrong. The titers of SARS-CoV-2 shedding from the URT is extremely high from the prodromal phase of illness until day 5 of the illness.[1]

The virus spread rate increases with the intensity of contact among members under the same roof. In that instance there was a spread rate of 75% in a study out of Germany.[2] Therefore, CoV-2 spreads easily. This reiterates the point that a preventative which can disable/kill CoV-2 needs to be used early by one who has been around others who have been infected—before they get any symptoms.

What is needed is a way to use a therapeutic agent that is safe for an individual, and an effective disabler/virucide that can be used on bacteria, fungi and viruses, particularly on SARS CoV-2, and its future mutants. This invention discloses a safe and effective agent, when used in certain ways, surprisingly kills Coronavirus while it is preferably in its incubation phase, in the URT. An active agent that fills that need is CLO2. Therefore, a discussion of CLO2 and SARS CoV-2 is appropriate.

A significant concern for any antiviral therapeutic is the potential for the virus to acquire drug resistance due to the rapid mutation of viral pathogens.[3] Such resistance becomes more obvious when selective pressure is applied in the setting of drug treatment. Vaccines that target the spike protein of SARS CoV-2 present a promising approach to combat COVID-19. But concerns remain that mutations can render the virus resistant to a vaccine. New spike mutants appear in the presence of individual antibodies, resulting in loss of neutralization. Such escape also occurred with combinations of antibodies binding diverse but overlapping regions of the spike protein. The spike protein is a key mediator of viral infectivity required for attachment and entry into target cells by binding the ACE2 receptor.

As mentioned above, a cocktail of different therapeutics and monoclonal antibodies would be welcomed because viral mutations would not make the Coronavirus immune to the monoclonal antibodies and future vaccines. A real problem for scientists is that the spike protein of the SARS CoV-2 does not have enough room for that needed third antibody. That statement comes from the President and CEO of Regeneron, who's double antibody cocktail was used to treat the President of the United States of America—Donald Trump.[4] For that reason, it is even more important to use CLO2 as a therapeutic. One way the virus is made inoperable by $CLO_2$, is through oxidation. Unlike monoclonal antibodies and future vaccine's which work only on the genetic codons and base pair sequencing, CLO2 can kill and disable CoV-2 in a number of ways, and not just by interrupting base pair sequencing—which it also does. CLO2 acts on that portion of CoV-2's spike protein known as the endodomain and takes up NO ROOM! This is discussed in more detail below.

With CLO2 no virus can become immune to it because it works to oxidize viruses. It has been used for over 100 years in wastewater with no generation of resistance, by any microbial pathogen. Furthermore, scientific evidence already exists that CLO2 kills the Coronavirus SARS CoV-2 (Fact Sheet, National Agricultural Biosecurity Center, Kansas State University) and other viruses in the Corona family.[5] Also, it has been specifically shown to be effective against human Coronavirus by BASF (BASF Aseptrol Label EPA Registration Number: 70060-19).

Vaccine development has focused on the spike glycoprotein, which mediates receptor recognition and membrane fusion. Coronavirus spike proteins have extensive glycosylation sites on each of three protein spikes. Ongoing vaccine development efforts have primarily focused on the spike proteins that protrude from the viral envelope and constitute the main target of neutralizing antibodies. These trimeric spike proteins mediate host cell entry with the spike1 and spike2 subunits responsible for binding to the host cell receptor and facilitating membrane fusion, respectively.[7] More recently, it has been disclosed that SARS CoV-2 attaches the same way: All CoVs encode a surface glycoprotein spike, which binds to the host-cell receptor and mediates viral entry. For Coronaviruses, a single region of the spike protein called the receptor-binding domain (RBD) mediates the interaction with the host-cell receptor. After binding the receptor, a nearby host protease cleaves the spike, which releases the spike fusion peptide, facilitating virus entry.[8]

Steric constraints prevent access of glycan processing enzymes to substrate glycans especially when the viral glycoprotein has evolved to mask the antigen with a particularly dense array of host-derived glycans. This restricts access to the glycan sites rendering glycan processing enzymes ineffective in the specific region of the antigen.[9]

CLO2 inactivates viruses by reacting with certain amino acids and denaturing the protein that contains those certain amino acids. In 1986, Noss et al. proved that CLO2 inactivated viruses due to its reactions with the viral capsid proteins. They found however, that three discrete chemical moieties in the viral protein, namely the cysteine, tyrosine, and tryptophan amino acid residues were able to react with $CLO_2$ rapidly.[10] In 2007 and 2012 Ogata found the same reactions on viruses by CLO2 as well.[11]

Although cysteine, tyrosine, and tryptophan residues are also found in human tissues, $ClO_2$ is much less toxic for humans or animals than for microbes (bacteria, fungi, and viruses). Nosztczius et al.[12] found that the main reason for this selectivity between humans and microbes is based not on their different biochemistries but on their different sizes. Based on experiments and calculations using a reaction-diffusion model, they found that the killing time of a living organism is proportional to the square of its characteristic size (e.g., its diameter), thus small ones will be killed extremely fast.

In this context it is interesting to remark that the spike protein of the new Coronavirus SARS_CoV-2 contains 54 tyrosine, 12 tryptophan, and 40 cysteine residues.[13] In the proximal portion of the spike (the endodomain), it has been found that the adjacent cysteine-rich region of the endodomain is critical for fusion of infected cells.[14]

As mentioned above; the protein coat is highly significant in viral infectivity and provides specificity for binding to the proper cell type. Two amino acids that would undergo oxidation and modification to a significant enough degree to permit inhibition of virus to cell binding are those containing sulfur—namely, methionine and cysteine.

The glycan coat hides the antigen and cloaks the spike in a polysaccharide, so that the human body's defense system does not recognize the spike as foreign. It is as a wolf in sheep's clothing, with the wolf's head being the epitope or antigen, at the end of the spike. CLO2 reacts with the rich cysteine area at the base, as well as the other cysteine residues quickly to denature the spike protein. This disables the SARS CoV-2's spike and exposes the stearic hidden antigen at the end of the spike. With this disabling, the virus is no longer able to be infective, and is exposed to the human immune system, where antibodies, and lymphocytes can be developed against it. That exposure also works as an adjunct to enable other therapeutics and vaccines to be more effective.

Another way that CLO2 destroys viruses, is by oxidizing the base guanine, found in both RNA and DNA viruses. The base is extremely sensitive to oxidation, forming 8-oxoguanine as the oxidation product.[15] The release of $CLO_2$ results in the oxidation product thereby disallowing the replication of the viral nucleic acid by base pairing. Although the replication of the protein coat may continue; the formation of a complete functional virus has been blocked by $CLO_2$ oxidation. Therefore, CLO2 can kill CoV-2 in a number of ways, but particularly by acting on the rich cysteine area in the endodomain which is responsible for the fusion of the virus, which CLO2 denatures in just seconds.

CLO2 decomposition products are sodium chloride (common table salt), water and oxygen,[16] hardly pathogenic to humans. Yet, CLO2 toxicity studies in man have been done. Daily ingestion of 500 ml $CLO_2$ having a concentration of 5 ppm is safely tolerated.[17] In other studies with rats the lethal dose (LD) of $NaCLO_2$ was established as 140 mg/kg.[18] In studies where $CLO_2$, $NaCLO_2$ or $CLO_3$ were included in the drinking water for up to several months, there were no significant increases in methemoglobin concentrations with doses as high as 1000 mg/liter (1000 ppm or 0.1%) in the rat, mouse or chicken.[19]

DETAILED DESCRIPTION OF THE INVENTION

Recently, this inventor discovered through the use of a CLO2 mouthwash on himself, that CLO2 would prevent the common cold. It can be used by any means of application; optically, orally but more preferably, nasally. It can be used as a gargle, as nasal drops, via a mister and/or with an atomizer, nebulizer such as Vios®, humidifier, vaporizer, fogger, a nasal wash bottle such as SinuCleanse® or a neti pot. To fight the common cold, preferably to prevent it, the CLO2 is used during the prodromal signs of a cold—runny nose, itching eyes, sneezing, etc. The common cold is caused by viruses other than a Coronavirus, such as a Rhinovirus, but the majority of colds are caused by the Coronavirus.[20] The virus incubates in the nose about 3 days for the common cold, and an average of 5 days, for COVID related to SARS, before spreading to other parts of the lower respiratory tract.

The CLO2 that is used is preferably an activated CLO2, as opposed to what is called stabilized CLO2 (SCD) which is a buffered, stabilized solution of sodium chlorite. If CLO2 is formed in SCD, it is reduced back to sodium chlorite by the added buffer. Those stabilized products have little to no microbiocidal activity.

SARS CoV-2 goes through an incubation period as do other Coronaviruses in its prodromal stage. Even though the incubation stage is an average of 5 days, it can be from 2-14 days.[21]

Studies show that SARS CoV-2 primarily incubates in the nose. In COVID-19, there is increasing evidence for the importance of sinus-nasal pathophysiology. The sinus-nasal cavity appears to be a major site of infection by SARS CoV-2, where susceptibility genes required for infection are expressed at high levels and may be modulated by environmental and host factors. Viral shedding appears to be the highest from the nose, therefore reflecting a major source for transmission. This has been highlighted by multiple reports of health care associated infection.[22]

It is in the cells of the nose, notably nasal epithelial cells, including clusters of goblet cells and ciliated cells, that show the highest expression among all investigated cells in the respiratory tree. Also, ACE2 expression in nasal epithelial cells have been confirmed in an independent study that included nasal brushings and biopsies. The results were consistent. Notably, their expression distribution coincided with viral transmissibility patterns based on a comparison to the basic reproduction number, which estimates the number of people who can become infected from a single infected person. The skewed distribution of the receptors/enzymes toward the upper airway is observed in viruses with higher infectivity, including those of SARS CoV and SARS CoV-2.[23]

SARS CoV-2's incubation is unlike the common cold, in that it has truly, little prodromal symptoms or signs, with the exception of a dry cough, sometimes fever, and a lost sense of smell. SARS CoV-2 like the Corona viruses before it, and surely the ones that will follow it, need a therapeutic treatment that is safe and effective—like CLO2—that can kill the virus or certainly attenuate it, in nasal and sinus mucous, particularly in its prodromal stage. The current invention should preferably be used in this prodromal phase, or routinely used as a preventative when a household member or a fellow health care worker are under the same roof with another person who has been infected by SARS CoV-2. This inventor himself had no symptoms after contracting SARS CoV-2. He later happened to find only a slight increase in his temperature.

In one aspect of the current invention, nasal drops with a concentration of CLO2 from 0.0003 ppm to 100 ppm are used as soon as there is a notice of an increase in one's temperature. More preferably a concentration of 0.01 ppm to 10 ppm concentration of CLO2 is used. Checking one's temperature throughout the day is impractical. But, for example, if one has a family member who has tested positive, or one who is a front-line defender, comes into contact with one who has already contracted a virus such as SARS CoV-2, or a future mutant, that person should start routinely using CLO2, even before his oral or forehead temperature increases. Again, this can be done because there is no downside risk since the decomposition products of CLO2 are common table salt, water and oxygen. One may use CLO2 in several ways as described herein.

Even though CLO2 is very safe when used properly, it can be dangerous when used in one particular way. Once Covid-19 is contracted, special considerations have to be taken if one is to use CLO2 as an inhalant—say as a fog from a nebulizer or atomizer, or as a mist from a sprayer. This is because the epithelial cells that separate the alveolar air from the blood stream are only 2 micrometers thick, and CLO2 gas can deplete through oxidation this precious, thin reductive barrier that separates the lung's air from bodily fluids. Those tissues, if damaged, could cause pneumonia. Fluids would then get into the lungs, causing one to drown in his own bodily fluids.

The invention is a two-part composition and is explained in detail below. One needs to be sure that an admixture of the composition will yield the proper amount of CLO2. The formula needs to be tweaked until it consistently yields the desired ppm of CLO2. After mixing the separate parts together CLO2 is formed. The CLO2 then complexes with unreacted chlorite to give a deeper green color than what it would be, if produced by the CLO2 alone. Therefore, in some photometric analysis techniques, the assay for CLO2 concentration can be interfered with by the CLO2/chlorite complex when it is formed. That can give a false reading for the concentration of CLO2 in the solution. For that reason, a recently developed electrochemical analytical technique known as chronoamperometry should be used. The instrument is known as the Kemio, by Palintest USA in Erlanger, Ky. It can accurately measure from 0-50 ppm of chlorine dioxide in only minutes.

Until science fully understands what concentration of CLO2, and its contact times with alveolar tissues are, we can only safely and very carefully use what science has already determined as safe exposure levels. OSHA has determined that a CLO2 concentration of 0.1 ppm concentration is safe for an 8-hour exposure, and a 0.3 ppm concentration is safe for a short-time exposure limit (STEL) of 15 minutes.[24]

Air inhaled by the average adult at rest, is about 12 breaths per minute, and about 1 liter (L) per breath. In 15 minutes, that would be about 180 L. If one uses 0.3 ppm concentration of CLO2, that would be equal to 54 micro liters. The math works out to be 0.15 mg of CLO2. If one inhaled 0.15 mg in a 15-minute period, then that would be only half of what is considered to be safe by OSHA. Safety is related to a time-weighted concentration. 15 minutes×a 0.3 ppm concentration would give 4.5 ppm minutes. If one were to inhale 4.5 ppm for 1 minute, one would take in the limit of 4.5 ppm minutes. It is reasonable then to assume that it would be safe to inhale an atomized solution of 4.5 ppm solution of CLO2, over a one-minute time period. That would then be, for an adult at restful respiration, inhaling 12 normal breaths of a 4.5 ppm concentration of CLO2. Since OSHA uses safety margins, one should be able to use even more than 4.5 ppm concentration of CLO2. Therefore, in one instance of the present invention, it is anticipated that a CLO2 concentration from say 0.01-10 ppm could be used as an aerosol spray, fog, gas or the like, which is generated by a nebulizer and is inhaled as a curative measure, even after COVID-19 is contracted. An adult dosage would be for one to inhale no more than 12 breaths each day, until studies have been done on laboratory animals showing that it is safe to inhale more than 12 breaths per day at a 5 ppm concentration. The other way the nebulizer could be used, is as this inventor used it when he had COVID-19. One takes a full, deep breath of air, then allows the nebulizer to pump the CLO2 vapor into his mouth only, being careful not to inhale, and slowly exhales the vapor through his nose. This way the CLO2 vapor can fill the sinus and nasal passages where the Coronavirus is, during its prodromal stage, killing it. To be on the stricter side of safety, this would be a preferable method of applying the CLO2 aerosol at this time.

The current inventor had a family member living under the same roof, who had been diagnosed as having COVID-19. As mentioned above, he had no signs or symptoms of having contracted SARS CoV-2, except for a slightly elevated temperature. He then began using a 5 ppm solution of CLO2 as nasal drops. He applied approximately 6 drops via a straw, 4 times per day. He placed 5 cc of the same 5 ppm concentration of CLO2 into the chamber of a Vios® nebulizer and created an aerosol fog. He took 3 slow, normal (at rest), 5-second inhalations, and waited one hour. Since no lung irritation had developed, he took 3 more. After 2 days, no lung irritation had developed, he then did 6 more 5-second inhalations/breaths and had no resulting lung irritation thereafter. He later developed a general malaise and had the feeling of being tired, so decided to get the polymerase chain reaction (PCR) test. He was found to have the SARS CoV-2 virus. Treatment using the nasal drops of 5 ppm CLO2, as described above, continued throughout for a total of 14 days. After 21 days he obtained a serology test, and it was confirmed that he had antibodies to SARS CoV-2. Even though he did contract SARS CoV-2, there were only little to slight symptoms—possibly the virus had been attenuated.

CLO2 works through mucosal tissue cells (the pseudo-stratified columnar epithelial cells with mucous producing goblet cells). That property makes it ideal to kill Coronaviruses in the sinus-nasal passages. This inventor, months before contracting SARS CoV-2, used CLO2 in the concentration mentioned above, as nasal drops only, to prevent the common cold. After the usual and normal prodromal signs of catching a common cold, the time one gets a runny nose, congestion etc., he prevented himself from catching one. Several drops were placed into each nostril 2 times per day, once in the morning, and once in the evening. Treatment was done 3 days beginning at the prodromal period. Nasal drops were allowed to run down through his nasal and oral pharynx as he rotated his head on his shoulders. Again, a cold never developed.

To generate a 5 ppm concentration of CLO2, one can use a 0.1% sodium chlorite concentration in a 16 oz bottle, containing approximately 475 cc of water, and activating it by potassium iodide to produce a CLO2 solution. Potassium iodide is an ideal activator because of its indefinite shelf life. Activation can be done with an oxychlorine species, such as using 2-3 drops of common household bleach such as Clorox (6% hypochlorite) in a 16-ounce solution of 0.1%.

Further Detailed Description of the Preferred Embodiment

The method of the present invention can have an initiator/activator of an alkali metal iodide, preferably potassium iodide (KI); with a composition containing an alkali metal chlorite, preferably sodium chlorite (NaClO2), in preferably an aqueous base; along with preferably, a buffer, an emulsifier, and a menthol such as peppermint to help open the sinuses. There may also be ingredients that loosen the mucous such as guaifenesin; and chemicals that are used to fight irritation like polyalcohols, such as glycerol, polyethylene glycol, propylene glycol; and antihistamines such as famotidine, hormones such as melatonin, steroids and corticosteroids such as dexamethasone. Other ingredients that can be used are generally those ingredients currently found in other nasal medications which act to be beneficial to a user.

Preferably, the sodium chlorite level is provided in excess, so escaping and/or reacting CLO2 can be replaced. Typically, the sodium chlorite is present in an amount from about 0.01% to about 5% by weight of the composition. The KI is present in an amount suitable to interact with the sodium chlorite to form CLO2. The CLO2 formation terminates in an equilibrium concentration.

The concentration achieved will depend on the precise concentration of each of the constituents in the composition. If for example, the total weight of an aqueous solution is to be 480 g, then about 2 g of a 25% sodium chlorite solution would be placed into 478 cc of water and would be activated by placing 0.07 g of KI and allowing the ingredients to set for 30 minutes while the CLO2 is formed.

The KI activator reacts with chlorite ion to form an intermediate. When the solution becomes slightly acidic, an equilibrium is established producing a steady state concentration of a second intermediate that can be stored for longer periods of time. In the presence of excess chlorite ion, the storable intermediate produces and maintains a relatively constant concentration of chlorine dioxide.

The method encompasses a two-part composition. Part 1 of the composition is on the basic side and has a useful concentration of sodium chlorite. One preferred solution of sodium chlorite is manufactured by Occidental Chemical Corporation located in Dallas, Tex. under the name "Technical Sodium Chlorite Solution 31.25". The 25% sodium chlorite solution has a pH of about 12.8.

Since the Part 1 composition of the invention uses a very much diluted 25% solution, then the pH is dropped from 12.8 to approximately 9.8. Some of the NaOH used to raise the pH up in the 25% solution is converted to NaCl (its end product), and the pH will further drop over time. Therefore, in one preferred embodiment, disodium phosphate is added to keep the composition buffered at a pH of 9.7 to prevent the premature activation of the sodium chlorite, which occurs near or below pH 7.

Part 2 of the composition is admixed with Part 1 at the time a useful concentration of ClO2 is desired. Part 2 contains a general, or protic acid, preferably phosphoric acid, which has some buffering capacity. In one preferred embodiment, monopotassium phosphate is used to decrease the pH of part 2 and buffer the final, activated ClO2 solution at a pH between 4 and 8 and more preferably about 6. ClO2 works throughout a broad pH range and can be also be activated or reactivated by a few drops of sodium hypochlorite (Clorox) within a minute of adding the hypochlorite to the chlorite solution. Part 2 can contain all the other ingredients which could cause premature activation producing chlorine dioxide, if mixed with the sodium chlorite. This is because even different flavors can produce activation if contained in the sodium chlorite solution of part 1. Truly little of each phosphate buffer is necessary. The disodium phosphate is about 0.02% of the base weight, and the monopotassium is about 11% of the activator weight. The preferred method of use of the invention is by treating nasal passages with drops, spray, aerosol, mist or fog. This way, it can be used throughout the day, like hand washing or hand sanitizing. One particular nebulizer that produces a fine aerosol fog that can be used is a Vios® nebulizer. It is currently used for example with patients suffering from asthma, COPD, and cystic fibrosis. The ways the ClO2 solution can be applied through the nose is by gravity, pressure, and suction.

Gravity allows the flow of ClO2 solution into the nasal cavity, for example, by inserting the tip of a teapot-like spout into one nostril and pouring the solution into it. The solution flows around the posterior margin of the nasal septum and out the other nostril. An example of that is a neti pot. Another way to apply the solution is to pump the solution into the nasal cavity, into one nostril, forcing it out and around the posterior margin of the nasal septum, and allowing it to drain out the other nostril. Another way is to pour the solution into a bottle cap and sniffing the solution down each nostril or using a straw to get solution down the nostrils. One simply inserts the straw into the solution about ⅜ of an inch, places his finger over the top of the straw, withdraws the straw from the solution, places it in the nostril, and removes his finger allowing the solution to run down the nostril. One can also use a bottle closure/cap by placing about 6-12 drops or more of the ClO2 solution inside the cap, then, placing the cap under the nostril and tilting one's head back and tilting the cap so as to allow the solution to enter the nostril. More preferably, one can use a bottle with a spouted tip or nasal plugged bottle to drip into the nostril or use a common pump type sprayer which is popularly used to spray solutions into the nose, as other medications are delivered today. Once the solution is in the nostril, again, one tilts his head back and rolls it around on his shoulders in order to spread the solution fully around in the nasal passages. The more preferable way to spread the solution is to lie on one's side with the parietal eminence of the skull resting on a flat surface such as a bed and administering the ClO2 solution into the lower nostril. This position is known in the medical literature as the lateral head low (LHL) position. The medical literature has found other good positions for patients administering medication such as the lying-head-back position (LHB) to effectively treat the sinus cavities. Patients are instructed to lie supine and hang their heads over the edge of their bed and point their nose to the ceiling, to best simulate this position. Finally, a solution of ClO2 can be used with a nebulizer by placing about 10 cc of the ClO2 solution in the nebulizer's chamber and creating a fog when the nebulizer's pump is turned on.

The method of generating a fog is done in a safe manner, not inhaling, but by exhaling only, as spoken of above. One hyperventilates by quickly inhaling and exhaling repeatedly, then taking a deep breath and holding it, using the nose or mouthpiece from the nebulizer; preferably the mouthpiece, turning on the nebulizer, and allowing ClO2 fog to be pumped into the oral cavity. One then slowly exhales through the nose allowing more time for the ClO2 fog to enter the nasal and paranasal passages.

The ClO2 solution can have fragrances to enhance the application, and to open up the different paranasal sinus passages. These passages can be more easily reached by using an aromatic such as peppermint, which has menthol. The peppermint opens up the sinus passages, and in a small proportion, reduces inflammation. Peppermint has been indicated as an interesting source for the development and discovery of new bioactive compounds with pharmaceutical and cosmetic applications due to its anti-inflammatory properties.[25] Peppermint is also an antioxidant. Truly little peppermint is used to open the sinus and nasal passages, to prevent the ClO2 from reacting with it. High doses of Vitamin C, a megadose far above the recommended daily allowance, should be avoided as it may react with the ClO2 before the ClO2 can react with a microbe.

If higher concentrations of ClO2 are desired—then a reducing sugar such as glucose or a non-hydroxylated aldehyde such as propionaldehyde, could be added to further increase ClO2 production. Also, even after activation, placing several drops of Clorox® can activate the solution further. Every 5 drops of it, approximately 0.2 grams, will increase the pH of a 16-ounce solution approximately 0.1 on the pH scale.

Finally, the product can be made for just pennies per 16 ounces, which is 8 to 16 times what is necessary for treatment. Countries around the world, rich and poor, can positively benefit from using a ClO2 solution, as outlined above. This inventor believes that he has shown that ClO2 can be a safe and effective therapeutic for the treatment of pathogens, and their corresponding pathologies. The invention will work not only on MRSA, the common cold, but especially on the current SARS CoV-2, its coming mutants and their corresponding pathologies such as COVID-19, and future COVIDs.

The invention is susceptible to various modifications and alternative forms. Specific examples and methods of use have been described herein, in detail. It is understood that the invention is not limited to the examples, methods, and solution concentrations alone; but on the contrary, its broad inventive concept is intended to cover all modifications,

[1] J Korean Med Sci. 2020 Apr. 6; 35(13): e142.
[2] Investigation of a COVID-19 outbreak in Germany resulting from a single travel-associated primary case: a case series, Merle M. Bohmer, PhD et al, THE LANCENT Infectious Diseases Volume 20, Issue 8, P876-877, Aug. 1, 2020
[3] A. Baum et al., Science 10.1126/science.abd0831 (2020),
[4] Schleifer, Leonard Dr., "Squawk Box", *Interview with Regeneron CEO*, CNBC, New Jersey, 2020 Oct. 5, Television
[5] Chlorine Dioxide, Part 1 A Versatile, High-Value Sterilant for the Biopharmaceutical Industry, Barry Winter et. al., Bioprocess International December 2005
[6] Zhou, Y., Jiang, S. & Du, L. Prospects for a MERS-CoV spike vaccine. Expert Rev. Vaccines 17, 677-686 (2018).
[7] Yuan, Y. et al. Cryo-EM structures of MERS-CoV and SARS-CoV spike glycoproteins reveal the dynamic receptor binding domains. Nat. Commun. 8, 15092 (2017).
[8] Letko, M., Marzi, A. & Munster, V. Functional assessment of cell entry and receptor usage for SARS-CoV-2 and other lineage B betacoronaviruses. *Nat Microbiol* 5, 562-569 (2020). https://doi.org/10.1038/s41564-020-0688-y
[9] Pritchard, L. K. et al. Glycan clustering stabilizes the mannose patch of HIV-1 and preserves vulnerability to broadly neutralizing antibodies. Nat. Commun. 6, 7479 (2015).
[10] Noss C I, Hauchman F S, Olivieri V P. Chlorine dioxide reactivity with proteins. *Water Res.* 1986; 20(3): 351-356, https://doi.org/10.1016/0043-1354(86)90083-7.
[11] Ogata N. Inactivation of influenza virus haemagglutinin by chlorine dioxide: oxidation of the conserved tryptophan 153 residue in the receptor-binding site. *J Gen Virol* 2012; 93: 2558-63, https://doi.org/10.1099/vir.0.044263-0.
[12] Noszticzius Z, Wittmann M, Kály-Kullai K, Beregvári Z, Kiss I, Rosivall L, Chlorine dioxide is a size-selective antimicrobial agent. *PloS One* 2013; 8(11): e79157, https://doi.org/10.1371/journal.pone.0079157.
[13] Tao Y, Queen K, Paden C R, Zhang J, Li Y, Uehara A, *Severe acute respiratory syndrome coronavirus* 2 isolate *2019-nCoV/USA-IL*1/2020, *complete genome. NCBI GenBank;* 2020. Available at https://www.ncbi.nlm.nih.gov/nucleotide/MN988713.1?report=genbank&log$=nuclalign&blast_rank=1&RID=304U21XH016.
[14] Genetic Analysis of Determinants for Spike Glycoprotein Assembly into Murine Coronavirus Virions: Distinct Roles for Charge-Rich and Cysteine-Rich Regions of the Endodomain Rong Ye, Cynthia Montalto-Morrison, Paul S. Masters DOI: 10.1128/JVI.78.18.9904-9917.2004
[15] de Souza-Pinto N C et al. (2001) Repair of 8-oxodeoxyguanosine lesions in mitochondrial DNA depends on the oxoguanine DNA glycosylase (OGG1) gene and 8-oxoguanine accumulates in the mitochondrial DNA of OGG1-defective mice. Cancer Res 61(14): 5378-5381.
[16] https://www.sciencedirect.com/topics/medicine-and-dentistry/sodium-chlorite
[17] Bianchine J R, Judith R L, Sudha C, Judy M (1982) Study of Chlorine Dioxide and Its Metabolites in Man National Service Center for Environmental Publications.
[18] (2014) Kirk-Othmer Encyclopedia of Chemical Technology. (3rd edn), McGraw-Hill Book Co, New York, USA, pp. 612.
[19] Abdel-Rahman M S, Couri D, Bull R J (1979) Kinetics of Chlorine Dixoide and Effects of Chlorine Drinking Water on Blood Glutathione and Hemolysis in Rat and Chicken. J Environ Pathol Toxicol 3(1-2): 431-449.
[20] Falsey A R, Rhinovirus and coronavirus infection-associated hospitalizations among older adults, J Infect Dis. 2002 May 1; 185(9):1338-41. Epub 2002 Apr. 16,
[21] Eu Suk Kim et al, Clinical Course and Outcomes of Patients with Severe Acute Respiratory Syndrome Coronavirus 2 Infection: a Preliminary Report of the First 28 Patients from the Korean Cohort Study on COVID-19J, Korean Med Sci. 2020 Apr. 6; 35(13): e142. Published online 2020 Apr. 1. doi: 10.3346/jkms.2020.35.e142
[22] Laryngoscope Investigative Otolaryngology, Isabelle Gengler M D et al., Sinonasal pathophysiology of SARS-CoV-2 and COVID-19: A systematic review of the current evidence, 5; 2020,354-359
[23] Sungnak, W., Huang, N., Bécavin, C. et al. SARS-CoV-2 entry factors are highly expressed in nasal epithelial cells together with innate immune genes. *Nat Med* 26, 681-687 (2020). https://doi.org/10.1038/s41591-020-0868-6
[24] US Occupational Safety and Health Administration, Determination of chlorine dioxide in workplace atmospheres, 1991, https://www.osha.gov/dts/sltc/methods/inorganic/id202/id202.html
[25] Lidiane Diniz do Nascimento et al, Bioactive Natural Compounds and Antioxidant Activity of Essential Oils from Spice Plants: New Findings and Potential Applications, Biomolecules. 2020 July; 10(7): 988. Published online 2020 July 10.3390/biom10070988

The invention claimed is:

1. A method of treating or attenuating a SARS CoV or SARS CoV-2 infection in a human comprising:
   a. a providing a nebulizer containing a therapeutic amount of chlorine dioxide (CLO2) in a solution or a nebulizer containing an amount of a solution with amounts of an alkali metal chlorite and an activator that are effective to produce the therapeutic amount of CLO2, and
   b. administering to the human through the oral cavity a fog comprising said therapeutic amount of CLO2 via an aerosol dispensed from said nebulizer,
   wherein the mouth of the human is placed on a mouth piece of said nebulizer prior to the administering; wherein, after the administration of the fog into the oral cavity, the human holds the fog in the oral cavity and then exhales through the nose to allow an effective portion of the fog to additionally enter the nasal and paranasal passages; and
   wherein the therapeutic amount of CLO2 provided by the nebulizer is at a concentration of 0.0003 to 100 ppm.

2. The method of claim 1, wherein said solution further includes adding at least one additional active agent selected from the group consisting of:
   a) a mucous loosening agent,
   b) an antihistamine,
   c) a decongestant,
   d) an anti-inflammatory agent,
   e) a polyalcohol,
   f) a steroid,
   g) a hormone,
   h) and combinations thereof.

3. The method of claim 1, wherein said solution contains about 0.1% sodium chlorite and develops about a 5 ppm CLO2 concentration, and further contains peppermint or menthol.

4. The method of claim 1, wherein the therapeutic amount of chlorine dioxide is produced by the solution containing said alkali metal chlorite and said activator, wherein said activator is selected from the group consisting of potassium iodide, sodium hypochlorite, aldehyde, reducing sugar, and combinations thereof.

5. A method of treating or attenuating a SARS CoV or SARS CoV-2 infection in a human comprising:
  a. providing the human with a solution containing amounts of an alkali metal chlorite and an activator that are effectively combined to produce a therapeutic amount of ClO2 in a ClO2 solution,
  b. administering to the human said therapeutic amount of the ClO2 in the ClO2 solution, wherein said ClO2 is at a concentration of 0.0003 to 100 ppm of the solution,
  c. allowing the administered therapeutic amount of ClO2 in the ClO2 solution to contact the paranasal passages and one or more of the nasal cavity, lungs and/or mouth;
  wherein the activator is a compound that is not an acid or chlorine,
  and wherein the administration is intranasal administration and/or administration by inhalation with a nebulizer having a mouth piece and/or nose piece.

6. The method of claim 5, wherein said ClO2 solution is contained in a teapot-like container, and the following steps are performed for administration:
  1) the tip of the teapot-like spout is inserted into the lower nostril of the human,
  2) the head of the human is turned completely sideways and said ClO2 solution is poured down the nasal passage via said teapot-like container that contains said ClO2 solution, by which the ClO2 solution flows by gravity into the nasal cavity,
  3) the human rolls the head back and around on the shoulders in order to spread the ClO2 solution fully around and down the nasal passage and through the nasal cavity and openings to the paranasal sinuses,
  4) the human next holds the head back to allow for the ClO2 solution to flow into the paranasal sinuses,
  5) the human tilts the head forward to allow the ClO2 solution to flow around the posterior margin of the nasal septum and out the other nostril, and
  6) the human repeats the steps 1-5 for the other nostril.

7. The method of claim 5, wherein the intranasal administration includes the steps of:
  1) pumping the ClO2 solution by a handheld squeeze bulb into a nasal cavity of the human,
  2) the head of the human is turned completely sideways and ClO2 solution continues to be pumped down the nasal passage via the lower nostril, forcing the ClO2 solution into the nasal cavity, while the human rolls the head on the shoulders in order to spread the ClO2 solution fully around and down the nasal passage and through the nasal cavity into the openings of the paranasal sinuses, and
  3) the human tilts the head forward to allow the ClO2 solution around the posterior margin of the nasal septum and out the other nostril.

8. The method of claim 5, wherein the intranasal administration includes the steps of:
  1) pouring said ClO2 into a cap,
  2) said cap is placed tightly under a nostril, where upon the human turns the head back as the ClO2 solution is poured and sniffed down the nostril,
  3) the human turns the head completely sideways placing the nostril with the ClO2 solution below the other nostril,
  4) the human rolls the head back and rolls the head upon the shoulders in order to spread the ClO2 solution fully around and down the nasal passage through the nasal cavity to the paranasal openings and into the paranasal sinuses,
  5) the human continues to hold the head back allowing said ClO2 solution to drain into the paranasal sinuses,
  6) the human tilts his head forward allowing the ClO2 solution around the posterior margin of the nasal septum and out the other nostril, and
  7) steps 1-6 are repeated for the other nostril.

9. The method of claim 5, wherein the intranasal administration includes the steps of:
  1) the human inserts a straw into said ClO2 solution, wherein the ClO2 solution contains 0.01 to 10 ppm of ClO2,
  2) the human places a finger over the top of the straw,
  3) the human withdraws the straw from the ClO2 solution and places the ClO2 solution in the straw into a nostril,
  4) the human removes the finger from the top of the straw to allow the ClO2 solution to run down the nostril,
  5) the human tilts the head back and rolls the head on the shoulders in order to spread the ClO2 solution fully around and down the nasal passage and through the nasal cavity into the openings of the paranasal sinuses,
  6) the human tilts his head forward to allow the ClO2 solution to run out of the nostril, and
  7) the human repeats steps 1-6 for the other nostril.

10. The method of claim 5, wherein the intranasal administration includes the steps of:
  1) pouring the ClO2 solution into a cap,
  2) placing the cap under a nostril,
  3) the human tilts the head back while also tilting the cap to allow the ClO2 solution to enter the nostril,
  4) the human rolls the head on the shoulders in order to spread the ClO2 solution fully around and down the nasal passage and through the nasal cavity into the openings of the paranasal sinuses, and
  5) the human repeats steps 1-4 for the other nostril.

11. The method of claim 5 wherein said ClO2 solution is placed into a bottle that has a spouted tip or nasal plug, wherein the intranasal administration includes the steps of:
  1) dripping the ClO2 solution from the bottle into a nostril,
  2) the human turns the head completely sideways placing the nostril with the ClO2 solution below the other nostril,
  3) the human rolls the head back and rolls the head upon the shoulders in order to spread the ClO2 solution fully around and down the nasal passage and through the nasal cavity into the openings of the paranasal sinuses,
  4) the human continues to hold the head back allowing said ClO2 solution to drain into the paranasal sinuses,
  5) the human tilts the head forward allowing the solution around the posterior margin of the nasal septum and out the other nostril, and
  6) the human repeats steps 1-5 for the other nostril.

12. The method of claim 5, wherein the intranasal administration includes the steps of:
  1) placing the ClO2 solution into a nostril,
  2) the human turns the head completely sideways placing the nostril with the ClO2 solution below the other nostril,
  3) the human rolls the head back and rolls the head upon the shoulders in order to spread the ClO2 solution fully around and down the nasal passage and through the nasal cavity into the openings of the paranasal sinuses,
4) the human continues to hold the head back allowing said CLO2 solution to drain into the paranasal sinuses,
5) the human tilts the head forward allowing the solution around the posterior margin of the nasal septum and out the other nostril, and
6) the human repeats steps 1-5 for the other nostril.

13. The method of claim 5, wherein the intranasal administration includes the steps of:
   1) placing the CLO2 solution into a nostril of the human and lying on the same side as the nostril containing said CLO2 solution with the parietal eminence of the head against a flat surface in a lateral head low position, and
   2) more of the CLO2 solution is inserted into the lower nostril while the human continues to lie on the parietal eminence on the side or more CLO2 solution is intranasally administered in another acceptable position for applying intranasal treatments, allowing the CLO2 solution to flow into the nasal cavity and through the paranasal opening and passageway to the paranasal sinuses to fill into the paranasal sinuses.

14. The method of claim 5, wherein the intranasal administration includes the steps of:
   1) the human lies supine and hangs the head over the edge of a bed,
   2) the human turns the head sideways, and
   3) the human places the CLO2 solution into the lower nostril allowing the CLO2 solution to flow into the nasal cavity and through the paranasal opening and passageway to the paranasal sinuses to fill into the paranasal sinuses.

15. The method of claim 5, wherein the administration by inhalation comprises:
   a. providing a nebulizer with the CLO2 solution or a nebulizer with the solution containing amounts of the alkali metal chlorite and the activator that are effectively combined to produce a therapeutic amount of CLO2 in the CLO2 solution, and
   b. administering to the human through the oral and/or nasal cavity a fog comprising said therapeutic amount of CLO2 via an aerosol dispensed from said nebulizer, wherein the mouth and/or nose of the human is placed a mouth piece and/or nose piece of said nebulizer prior to the administering; wherein, after the administration of the fog through the nose piece and/or the mouth piece, the human takes breaths to inhale the fog containing the therapeutic amount of CLO2; and wherein the therapeutic amount and time of CLO2 provided by the nebulizer is at a concentration-time weighted level of 5 ppm-minutes.

16. The method of claim 5, wherein said activator is selected from the group consisting of potassium iodide, sodium hypochlorite, aldehyde, reducing sugar, and combinations thereof.

17. The method of claim 5, wherein the treatment begins when a worker or family member has been in contact with another who has COVID-19, and is treated with the therapeutic amount of CLO2 at a concentration-time weighted level of 5 ppm-minutes and the therapeutic amount of CLO2 is at a concentration of 0.01 to 10 ppm.

18. A method of treating or attenuating a SARS CoV or SARS CoV-2 infection in a human comprising:
   a. providing a nebulizer containing a therapeutic amount of CLO2 in a solution or a nebulizer containing a solution with amounts of an alkali metal chlorite and an activator that are effective to produce the therapeutic amount of CLO2, and
   b. administering to the human through the oral and/or nasal cavities a fog comprising said therapeutic amount of CLO2 via an aerosol dispensed from said nebulizer, wherein the mouth and/or nose of the human is placed on the mouth piece and/or nose piece of said nebulizer prior to the administering; wherein, after the administration of the fog through the mouthpiece and/or nosepiece, the human takes breaths to inhale the fog containing the CLO2; wherein the therapeutic amount of CLO2 provided by the nebulizer is at a concentration of 0.0003 to 10 ppm, wherein the concentration-time weighted level of administered CLO2 is equivalent to a value from the range of about 4.5 ppm-minutes to about 5 ppm-minutes.

19. The method of claim 18, wherein the treatment is done over a period of about 15 minutes to about 8 hours.

* * * * *